US00PP24865P3

(12) United States Plant Patent
Danziger

(10) Patent No.: US PP24,865 P3
(45) Date of Patent: Sep. 9, 2014

(54) ***IMPATIENS* PLANT NAMED 'DHAR397'**

(50) Latin Name: *Impatiens hawkeri*
Varietal Denomination: DHAR397

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 82 days.

(21) Appl. No.: 13/694,384

(22) Filed: Nov. 26, 2012

(65) Prior Publication Data

US 2014/0150146 P1 May 29, 2014

(51) Int. Cl.
*A01H 5/00* (2006.01)

(52) U.S. Cl.
USPC ..... Plt./318.6

(58) Field of Classification Search
USPC ..... Plt./318.6
See application file for complete search history.

*Primary Examiner* — Annette Para
(74) *Attorney, Agent, or Firm* — Cassandra Bright

(57) ABSTRACT

A new and distinct *Impatiens* cultivar named 'DHAR397' is disclosed, characterized by large pinkish center and magenta margin. The new variety has a compact growth habit and good branching. The new variety is an *Impatiens*, normally produced as an outdoor garden or container plant.

2 Drawing Sheets

Figure 1:
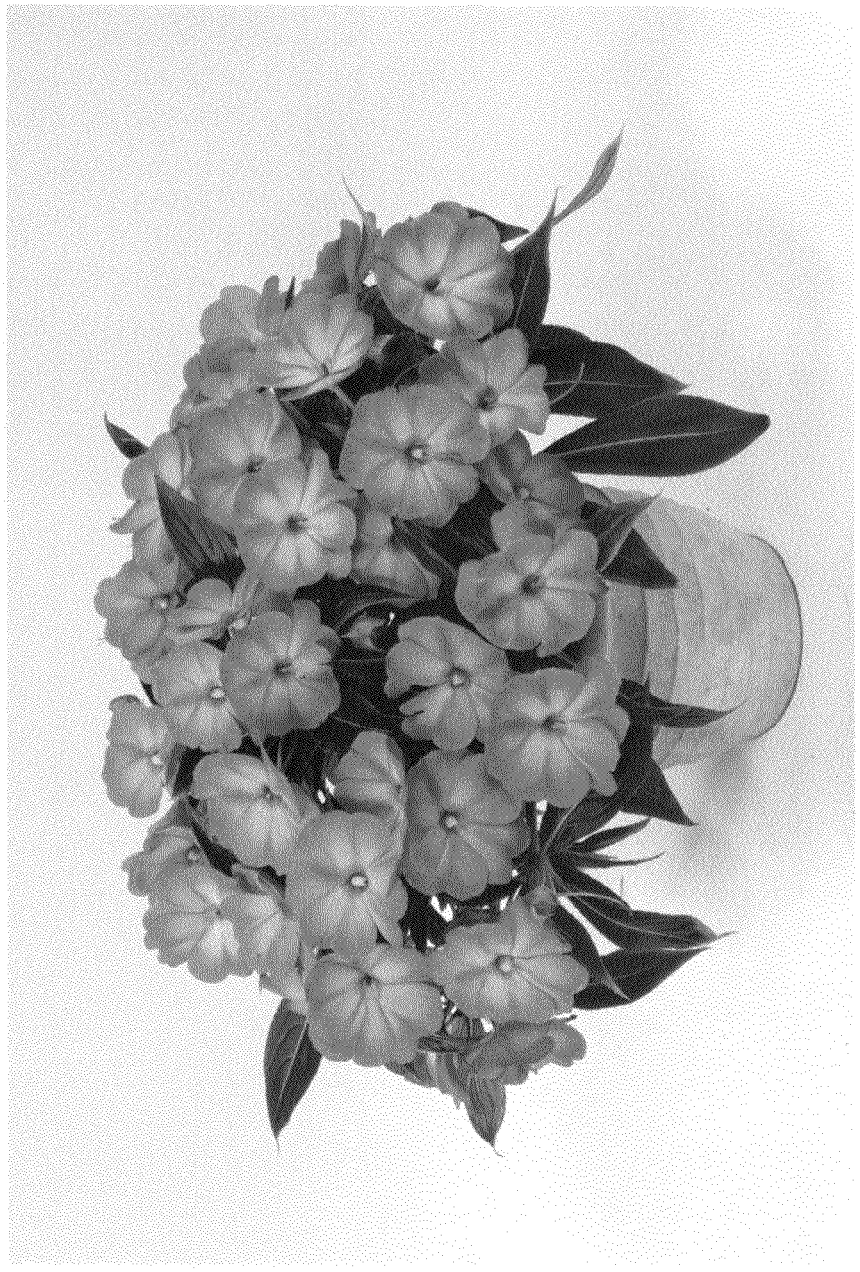

Latin name of the genus and species: *Impatiens hawkeri.*
Variety denomination: 'DHAR397'.

BACKGROUND OF THE INVENTION

The new *Impatiens* cultivar is a product of a planned breeding program conducted by the inventor, Gavriel Danziger, in Moshav Mishmar Hashiva, Israel. The objective of the breeding program was to produce new *Impatiens* varieties for ornamental commercial applications. The cross resulting in this new variety was made during January of 2010.

The seed parent is the unpatented, proprietary seedling variety referred to as *Impatiens hawkeri* 'NG-8-8707' The pollen parent is the unpatented, proprietary seedling variety referred to as *Impatiens hawkeri* 'NG-6-4720'. The new variety was discovered in July of 2010 by the inventor in a group of seedlings resulting from the 2010 crossing, in a research greenhouse in Moshav Mishmar Hashiva, Israel.

Asexual reproduction of the new cultivar was performed by leaf cuttings. The cuttings are from an apical bud that has no more than two expanded leaves and three to four immature leaves present. This was first performed at a research greenhouse in Moshav Mishmar Hashiva, Israel in August of 2010 and has shown that the unique features of this cultivar are stable and reproduced true to type in successive generations.

SUMMARY OF THE INVENTION

The cultivar 'DHAR397' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DHAR397' These characteristics in combination distinguish 'DHAR397' as a new and distinct *Impatiens* cultivar:

1. The flowers have a unique magenta margin.
2. Large pinkish center.
3. Good Branching.
4. Compact growth habit.

Plants of the new cultivar 'DHAR397' are similar to plants of the seed parent, *Impatiens hawkeri* 'NG-8-8707' in most horticultural characteristics, however, plants of the new cultivar 'DHAR397' produce a magenta margin whereas the seed parent has a pink margin. 'DHAR397' also has a pinkish center whereas seed parent has a white center. 'DHAR397' has a more compact growth form than the seed parent.

Plants of the new cultivar 'DHAR397' are similar to plants of the pollen parent; *Impatiens hawkeri* 'NG-6-4720' in most horticultural characteristics, however, plants of the new cultivar 'DHAR397' produce larger flowers and begin blooming earlier than the pollen parent. 'DHAR397' also produces a magenta margin whereas pollen parent produces an orange margin.

COMMERCIAL COMPARISON

Plants of the new cultivar 'DHAR397' are comparable to the variety *Impatiens* 'DANHAR305' U.S. Plant Pat. No. 21,306. The two *Impatiens* varieties are similar in most horticultural characteristics; however, the new variety 'DHAR397' differs in having larger white center and is more vigorous.

Plants of the new cultivar 'DHAR397' can also be compared to the commercial variety *Impatiens* 'DANHAMAG' unpatented. These varieties are similar in most horticultural characteristics; however 'DHAR397' has a larger white center and is more vigorous.

BRIEF DESCRIPTION OF THE PHOTOGRAPHS

The accompanying photograph in FIG. 1 illustrates in full color a typical plant of 'DHAR397' grown in a greenhouse, in a 12 cm basket. Age of the plant photographed is approximately 3 months from a rooted cutting.

Figure 2:
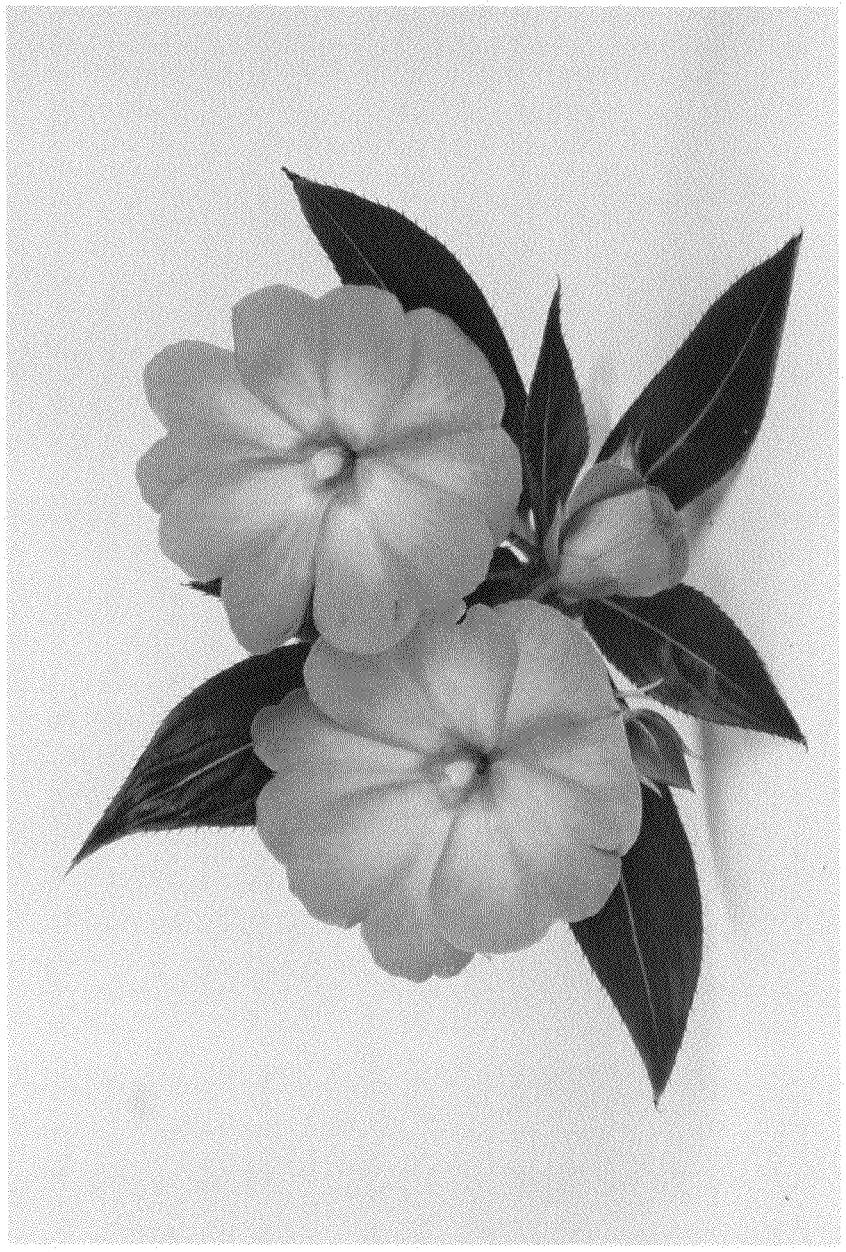

FIG. 2 illustrates in full color a close up of a typical bloom of 'DHAR397'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'DHAR397' plants grown in a greenhouse, in Moshav Mishmar Hashiva, Israel. The growing temperature ranged from 20° C. to 30° C. during the day and from 15° C. to 20° C. during the night. General light conditions are bright, normal sunlight. Measurements and numerical values represent averages of typical plant types.

Botanical classification: *Impatiens hawkeri* 'DHAR397'.

PROPAGATION

Time to initiate roots: Summer: About 7 to 10 days at approximately 25° C. Winter: About 10 to 14 days at approximately 20° C.

Root description: Fine, adventitious fibrous.

PLANT

Age of plant described: Approximately 84 days from a rooted cutting.

Growth habit: Round and compact with very good branching.

Pot size of plant described: 12 cm.

Height: 17 cm.

Plant spread: 30 cm.

Growth rate: Medium.

Branching characteristics: Highly branched.

Length of primary lateral branches: 14 cm.

Quantity of primary lateral branches: 8.

Characteristics of primary lateral branches:

- *Form*.—Oval shape.
- *Diameter*.—0.8 cm.
- *Color*.—Green 144 A RHS.
- *Texture*.—Smooth.
- *Strength*.—Strong, very stable.

Internode length: 3.0-4.0 cm.

FOLIAGE

Leaf:

- *Arrangement*.—Alternate.
- *Quantity*.—Approximately 15-18 per branch.
- *Average length*.—7.5 cm.
- *Average width*.—3.5 cm.
- *Shape of blade*.—Lanceolate to ovate.
- *Apex*.—Attenuate.
- *Base*.—Acuiminate.
- *Margin*.—Ciliate.
- *Texture of top surface*.—Smooth.
- *Pubescence*.—None.
- *Aspect*.—45 degrees.
- *Color*.—Young foliage upper side: Green 137 B RHS. Young foliage under side: Green 138 B RHS. Mature foliage upper side: Green 147 A RHS. Mature foliage under side: Green 147 B RHS.
- *Venation*.—Midrib with secondary veins. Pinnate, only lower surface. Type: Pinnate. Venation color upper side: Midrib Greyed-White 156C RHS. Venation color under side: Midrib Yellow-Green 147 D RHS. Venation: Yellow-Green 147 C.
- *Petiole*.—Length: 1.5 cm. Diameter: 0.5 cm. Color: Yellow-Green 146D. Texture: Smooth.

FLOWER:

Natural flowering season: Flowers at any day length. All year round in a greenhouse environment. Flowering is continuous from spring until fall in an outdoor garden.

Days to flowering from rooted cutting: 9-10 Weeks.

Inflorescence and flower type and habit: Single flowers raised above the foliage. The corolla consists of five petals.

Rate of flower opening: 10 to 15 days from bud to fully opened flower.

Flower longevity on plant: 5-7 days.

Persistent or self-cleaning: Self-Cleaning.

Bud:

- *Shape*.—Ovate.
- *Length*.—1.5 cm.
- *Diameter*.—1 cm.
- *Color*.—Red Purple Group 69B.

Flower size:

- *Diameter*.—6.0 cm.
- *Depth*.—0.3 cm.

Petals:

- *Quantity*.—5.
- *Arrangement*.—Overlapping.
- *Length*.—3.0 cm.
- *Width*.—2.5 cm.
- *Shape*.—Round.
- *Apex*.—Heart Shape.
- *Base*.—Acute.
- *Margin*.—Entire.
- *Texture, upper and lower surfaces*.—Smooth.
- *Color*.—When opening, upper surface: Margin Red Group 50A; Center Red Purple Group N66D. When opening, lower surface: Margin Red Purple Group 73C; Center Red Purple Group 58D. Fully opened, upper surface: Margin Red Group 50A; Center Red Purple Group N66D. Fully opened, lower surface: Red Group 55A.

Spurs:

- *Quantity per flower*.—1.
- *Length*.—5 cm.
- *Diameter*.—0.1 cm.
- *Aspect*.—Spur curvature 40°- 45° from peduncle.
- *Color*.—Towards base: Light Red Pink Group 49 D RHS.
- *Apex*.—Yellow Green Group 149 D RHS.

Sepals:

- *Quantity*.—2.
- *Length*.—1.2 cm.
- *Width*.—0.5 cm.
- *Shape* (*overall*).—Oblong. Apex: Acute. Base: Rounded.
- *Margin*.—Entire.
- *Color*.—Green group 142 B.

Peduncles:

- *Length*.—5.0 cm.
- *Diameter*.—0.1 cm.
- *Angle*.—About 45° to the lateral branch.

*Strength*.—Stable, flexible.
*Texture*.—Smooth.
*Color*.—Yellow Green Group 145A.
Fragrance: None.

REPRODUCTIVE ORGANS

Stamens:
*Number*.—There are five stamens with introrse anthers that are more or less fused and form a cap over the ovary.
Anthers:
*Shape*.—Oblong.
*Length*.—Approximately 0.5 cm.
*Color*.—White group 155D.
*Pollen*.—Color: White group 155D. Quantity: Abundant.

Pistil:
*Number*.—1.
*Length*.—0.5 cm.
*Style*.—Length: 0.4 cm. Color: Yellow Green group 146C.
*Stigma*.—Shape: Round. Color: Yellow Green 2D. Ovary Color: Yellow-Green group, 144D.

OTHER CHARACTERISTICS

Seeds and fruits: 10 to 20 minute dust like seeds present.
Disease/pest resistance: Common to cultivar.
Temperature tolerance: Tolerant at 30° C. and tolerant at 10° C. degrees Celsius (grows best at 18° C.-25° C.).

What is claimed is:

1. A new and distinct cultivar of *Impatiens* plant named 'DHAR397' as herein illustrated and described.

* * * * *